US011406757B2

(12) United States Patent
Friedli et al.

(10) Patent No.: US 11,406,757 B2
(45) Date of Patent: Aug. 9, 2022

(54) CONTROLLER AND METHOD FOR REFILLING A DOSING UNIT

(71) Applicant: Roche Diabetes Care, Inc., Indianapolis, IN (US)

(72) Inventors: Kurt Friedli, Mannheim (DE); Stefan Pfalz, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 110 days.

(21) Appl. No.: 16/785,579

(22) Filed: Feb. 8, 2020

(65) Prior Publication Data

US 2020/0171237 A1 Jun. 4, 2020

Related U.S. Application Data

(63) Continuation of application No. PCT/EP2018/071474, filed on Aug. 8, 2018.

(30) Foreign Application Priority Data

Aug. 9, 2017 (EP) ..................................... 17185472

(51) Int. Cl.
*A61M 5/168* (2006.01)
*G16H 20/17* (2018.01)
*A61M 5/145* (2006.01)
(52) U.S. Cl.
CPC ...... *A61M 5/16809* (2013.01); *A61M 5/1452* (2013.01); *A61M 5/16881* (2013.01); *G16H 20/17* (2018.01); *A61M 2205/3386* (2013.01)
(58) Field of Classification Search
CPC ............ A61M 5/16809; A61M 5/1452; A61M 5/16881; A61M 2205/3386;
(Continued)

(56) References Cited

U.S. PATENT DOCUMENTS

2010/0049127 A1 2/2010 Haueter et al.
2014/0039392 A1* 2/2014 Geipel .............. A61M 5/14216
604/123
(Continued)

FOREIGN PATENT DOCUMENTS

EP 1 970 677 A1 9/2008
RU 2 575 307 C2 2/2016
WO WO 2012/140063 A1 10/2012

OTHER PUBLICATIONS

International Search Report and Written Opinion of the International Searching Authority, PCT/EP2018/071474, dated Sep. 12, 2018, 10 pages.

*Primary Examiner* — Nilay J Shah
(74) *Attorney, Agent, or Firm* — Bose McKinney & Evans LLP

(57) ABSTRACT

Disclosed is a method for scheduling a refilling of a secondary reservoir of an ambulatory infusion system out of a primary reservoir storing a liquid drug. The method includes repeatedly and automatically carrying out a filling volume assessment routine. The filling volume assessment routine includes: determining, at a present point in time, an estimated filling volume of the secondary reservoir at a future estimation point in time, the future point in time being an estimation time interval after the present point in time, and determining in dependence of the estimated filling volume, if the secondary reservoir shall be refilled at the present point in time.

25 Claims, 3 Drawing Sheets

(58) Field of Classification Search
CPC .......... A61M 2005/3114; A61M 5/204; A61M 2205/3396
See application file for complete search history.

(56) References Cited

U.S. PATENT DOCUMENTS

| | | |
|---|---|---|
| 2014/0039396 A1 | 2/2014 | Gelpel et al. |
| 2017/0100537 A1 | 4/2017 | Haueter et al. |
| 2017/0100546 A1 | 4/2017 | Haueter et al. |

\* cited by examiner

CONTROLLER AND METHOD FOR REFILLING A DOSING UNIT

RELATED APPLICATIONS

This application is a continuation of PCT/EP2018/071474, filed Aug. 8, 2018, which claims priority to EP 17 185 472.2, filed Aug. 9, 2017, the entire disclosures of both of which are hereby incorporated by reference herein.

BACKGROUND

This disclosure relates to the field of infusion devices and infusion systems for liquid drugs. It particularly relates to the filling scheduling of a secondary reservoir out of a primary reservoir for subsequent infusion out of the secondary reservoir over an extended time period.

Ambulatory infusion devices are well known in the art for example in the therapy of Diabetes Mellitus by Continuous Subcutaneous Insulin Infusion (CSII) as well as in pain therapy or cancer therapy and are available from a number of suppliers. Throughout this document, a design that is particularly suited for CSII is generally assumed for exemplary purposes.

Ambulatory infusion devices that are used for CSII are designed to be carried by a Person with Diabetes (PwD), also referred to as "user," generally continuously night and day. The devices are designed to be carried concealed from view, e.g., with a belt clip or in a pocket, and/or may be designed to be alternatively carried directly attached to the body via an adhesive pad. Ambulatory infusion devices are designed to infuse liquid drug, in particular insulin, in at least two ways. First, they are designed to infuse liquid drug substantially continuously according to a typically pre-programmed and time variable basal infusion schedule autonomously, i.e., without requiring particular user interactions or operations. Second, they are designed to infuse larger drug boli on demand, for example to compensate for the intake of carbohydrates as well as to correct undesired high blood glucose values. To control these and optional further functions, ambulatory infusion devices comprise an electronics control unit, typically based on one or more microprocessors, in particular, microcontrollers. Throughout this document, the expressions "ambulatory infusion device" and "ambulatory infusion system" refer to a device and system respectively with at least the before-described basic functionality. "Respectively" is used in this specification in some instances to mean "in particular."

According to a classic and well-established design, ambulatory infusion devices or systems are typically of the syringe-driver type where liquid drug is infused out of a liquid drug cartridge by way of controlled and incremental displacement of a cartridge piston. For displacing the cartridge piston, a spindle drive with an electric motor is provided. Typical cartridge volumes are in a range of, e.g., 1 ml to 3 ml and store liquid drug, in particular insulin, for a number of days up to a week or more. A number of drawbacks of such devices is known in the art. In particular, they have a limited precision because they involve delivering very small drug amounts, typically in the nanoliter range, out of a drug cartridge having an overall drug volume in the milliliter range. Therefore, additional concepts and architectures have been proposed which use a dedicated dosing unit downstream from the drug reservoir. The dosing unit comprises, e.g., a micro membrane pump or a micro piston pump and is adapted to couple to a drug reservoir. The dosing unit is especially designed for precise metering of small volumes. While several designs for such dosing units are known in the art, they are rather complex, and most of them are expensive and/or critical with respect to large-scale manufacture.

EP1970677A1 discloses a system with a miniaturized metering piston pump with a dosing cylinder that is repeatedly fluidically coupled to and filled from a larger reservoir, followed by fluidically coupling the dosing cylinder to an infusion site and infusing the liquid drug out of the dosing cylinder in incremental steps and over an extended time period. For alternatively coupling the dosing cylinder to the reservoir and the infusion site, a valve system or valve unit is proposed. The infusion is a metered infusion of controlled volumes respectively volume increments.

Throughout the document, an architecture in accordance with the principles of EP1970677A1 is assumed. The larger reservoir is also referred to as a "primary reservoir" and stores liquid drug for a number of days up to a week or more as explained before. The dosing cylinder is referred to as a "secondary reservoir." Out of the dosing cylinder, liquid drug is infused in substantially the same way as is the case for the above-described classic syringe-driver design. Both the valve switching and the displacement of a piston in the secondary reservoir, and the valve switching are controlled by way of an electronic control unit.

In contrast to a classic syringe-driver, the filling volume of the secondary reservoir is comparatively small and may, by way of example, be 70 microliters, corresponding to 7 I. U. (International Units) of a liquid insulin formulation of standard concentration U100.

Whenever the secondary reservoir is empty or approaching emptiness, refilling out of the primary reservoir is required for continuing the infusion. Monitoring the filling state of the secondary reservoir and refilling it as required is desirably a background process that is controlled and executed by the ambulatory infusion device autonomously, without requiring user involvement. For a number of reasons and constraints related to the device design and energy consumption, the filling and refilling of the secondary reservoir is favorably carried out comparatively slowly and may require a time in a range of, e.g., 1 minute or more.

WO 2012/140063 A1 discloses an ambulatory infusion device and a method for operating such device which includes the steps of: (a) determining a maximum refill level for the secondary reservoir, based on given external parameters, wherein the maximum refill level does not exceed the maximum capacity of the secondary reservoir; (b) filling the secondary reservoir with liquid medicament from the primary reservoir to the maximum refill level; (c) metering and conveying the multitude of portions of liquid medicament to the downstream conduit; (d) if the secondary reservoir becomes empty, refilling the secondary reservoir as in step (b) and continuing with step (c).

In the context of an ambulatory infusion device and ambulatory infusion system with a primary reservoir and a secondary reservoir as explained before, unnecessary refilling steps should generally be avoided since each refilling is associated with considerable energy consumption and potentially introduction of some dosing error because of the valve switching and directional changes of the piston movement. Further, it is desirable to infuse drug boli, as far as possible, without the need to refill the secondary reservoir in between. That is, a refilling of the secondary reservoir during the bolus infusion should be avoided.

This disclosure teaches managing and scheduling the refilling of the secondary reservoir such that the refilling is carried out at particularly suited points in time. Particularly suited points in time are such times where the therapeutically relevant operation of the ambulatory infusion device, in particular the basal and bolus infusion, is not affected, or the effect is at least small. Advantageously, unnecessary refilling procedures are avoided.

In a general way, managing of the secondary reservoir is achieved by forecasting respectively predicting the volume of liquid drug that is expected to be infused in the near future and determining the points in time for the refilling based on said prediction.

In an aspect, a method is disclosed for scheduling a refilling of a secondary reservoir of an ambulatory infusion system out of a primary reservoir. The primary reservoir stores a liquid drug. The method includes repeatedly and automatically carrying out a filling volume assessment routine. The filling volume assessment routine includes, at a present point in time, determining an estimated filling volume of the secondary reservoir at a future estimation point in time and determining, in dependence of the estimated filling volume, if the secondary reservoir shall be refilled at the present point in time. The future point in time is an estimation time interval after the present point in time. That is, the estimation time interval is the time difference between the future point in time and the present point in time.

The estimated filling volume is a predicted filling volume and is the filling volume of the secondary reservoir that is to be expected at the estimation point in time if drug is infused out of the secondary reservoir from the present point in time to the estimation point in time without the secondary reservoir being refilled.

Via the method, it is determined whether the secondary reservoir should be refilled immediately, i.e., at the present point in time in order to avoid the need for refilling at a potentially unsuitable future point in time, in particular at a point in time where drug administration shall be carried out and the remaining filling volume of the secondary reservoir is likely to be not sufficient.

The method for scheduling the refilling is typically implemented as computer-implemented method and is executed by way of one or more microcomputer(s) and/or microcontroller(s) that execute(s) corresponding software or firmware code.

The estimated filling volume is an estimator for the filling volume of the secondary reservoir at the estimation point in time. In some embodiments, the filling volume assessment routine includes determining the estimated filling level, in particular, estimated filling volume by subtracting an infusion estimator from the filling volume of the secondary reservoir at the present point in time, the infusion estimator being an estimator for the amount of drug that is expected to be infused in the estimation time interval. The infusion estimator may include a dedicated basal infusion estimator and a dedicated bolus infusion estimator for combined basal and bolus infusion, as explained further below. Alternatively, the infusion estimator may be a combined infusion estimator that reflects the total infusion, both bolus and basal.

The estimation time interval is a time interval for which the drug administration out of the secondary reservoir can be predicted respectively estimated with sufficient certainty as explained further below in more detail. It is noted, however, that a precise prediction is not necessarily required since the secondary reservoir may be refilled out of the primary reservoir at any time, if required. In the context of CSII, the estimation time interval may, e.g., be 2 hours. Longer or shorter time intervals, such as 1 hour or 4 hours, may be used as well. Typically, the estimation time interval is predetermined and constant. In further embodiments, however, the estimation time interval is not predetermined but adaptive. As a general rule, the estimation time interval may be long if the predictability is high, that is, if the profile of basal and/or bolus infusion as a function of time of day is constant or similar over an extended time period of, e.g., a number of days or weeks. If the predictability, in contrast, is low, shorter estimation time intervals may be favorable. In an embodiment, the method includes repeatedly determining the variability of the profile of past basal and/or bolus infusion by way of statistical analysis and modifying the estimation time interval in dependence of the determined variability.

In some embodiments, the method includes carrying out the filling volume assessment routine at time intervals of a duration that is shorter than the estimation time interval. The filling volume assessment routine may be carried out with a fixed time interval, of, e.g., 10 minutes. Longer or shorter time intervals, such as 5 minutes, 30 minutes, or 60 minutes may also be used. In typical embodiments, the steps are carried out at predetermined specific times of day. In alternative embodiments, the times of day at which the filling volume assessment routine is carried out are, at least partly, not predetermined but different for different times of day. As a general rule, the filling volume assessment routine may be carried out less often at times of day where the predictability of the basal and/or bolus infusion is high and more often at times of day where the predictability is low. By way of example, the filling volume assessment routine may be carried out more often during daytime and less often during night time. Further, the filling volume assessment routine may optionally be synchronized with the basal infusion. For ambulatory infusion devices with substantially continuous basal infusion in incremental doses as explained further below, it may, e.g., be generally carried out substantially subsequent to an incremental basal infusion, thereby ensuring a maximum available time interval for the refilling of the secondary reservoir and consequently avoiding interference with the next following incremental infusion.

Alternatively or preferably additionally to carrying out the filling volume assessment routine according to a schedule, the method may include carrying out the filling volume assessment routine upon occurrence of a trigger event. Such trigger event may, e.g., be a temporary user-commanded modification of the predetermined basal infusion schedule or the cancelling of such modification, and/or the occurrence of a therapy-related event which has an impact on the infusion, such as a situation of low blood glucose as explained further below in more detail. Further, the programing of an on-demand bolus infusion may serve as trigger event.

The filling volume assessment routine is a background routine that is carried out with a time interval as discussed before during regular operation of the ambulatory infusion system, where basal and/or bolus infusions are carried out. The points in time where the filling volume assessment routine is carried out are current points in time.

In some embodiments, the method includes, as part of the filling volume assessment routine, determining that the secondary reservoir shall be refilled if the estimated filling volume is below a filling volume threshold. Typically, the filling volume threshold is predetermined. In some embodiments of this type, the filling volume threshold is zero, that is, it is determined that the secondary reservoir should be refilled at the present point in time if the estimated filling volume is negative. In this context, it is to be understood that a negative physical filling volume is impossible for technical reasons. Alternatively, the filling volume threshold is not zero but positive and considers, e.g., some safety margin. In such embodiment, the filling volume threshold may, for the case of CSII, e.g., be in a range of 10 microliters to 50 microliters, respectively 1 IU to 5 IUs (International Units) of a liquid insulin formulation of standard concentration U100. A positive filling volume threshold may in particular correspond at least to a back-dosing volume as explained further below.

In some embodiments, the method includes, as part of the filling volume assessment routine, determining that the secondary reservoir shall not be refilled if the estimated filling volume is below the filling volume threshold, but an expected duration to the next administration of an on-demand bolus exceeds a bolus timeout threshold. For this type of embodiment, the secondary reservoir may not be refilled at the present point in time even though it should, in principle, be refilled based on the estimation as explained before. In particular, the secondary reservoir is not refilled for this type of embodiment if the time interval from the present point in time to the predicted or expected point in time for the next on-demand bolus exceeds the bolus timeout threshold. The bolus timeout threshold is typically predetermined and may, e.g., be 20 min according to a specific example. This type of embodiment avoids a refilling that may in fact be unnecessary due to typical variability in drug infusion. In particular, the bolus timeout threshold corresponds to a time interval beyond which the estimated filling volume of the secondary reservoir has a significant likelihood of substantially deviating and being in particular above the estimated filling volume. Typical reasons for such deviation may be that basal infusion is temporarily reduced or suspended because of a physical activity or low blood glucose. Further, if there is a long time to the next bolus as expected, there is some likelihood that the bolus will in fact not be infused as expected.

In some embodiments of the before-described type, the method includes, as part of the filling volume assessment routine, determining that the secondary reservoir shall not be refilled if the estimated filling volume is below the filling volume threshold, the expected duration to the next following administration of an on-demand bolus does not exceed the bolus timeout threshold, but an expected bolus volume of the next following on-demand bolus does not exceed a bolus volume threshold. In a situation where the estimated filling volume is below the filling volume threshold and the expected duration to the next following administration of an on-demand bolus does not exceed the bolus timeout threshold, the secondary reservoir should generally be refilled as explained before. For the here-described type of embodiment, however, the secondary reservoir is not refilled under these conditions if the expected bolus volume of the next following on-demand bolus does not exceed the bolus volume threshold. In a typical embodiment, the bolus volume threshold corresponds to the filing level of the secondary reservoir at the present point in time, optionally including a safety margin. The safety margin may at least correspond to a back-dosing volume. For this type of embodiment, the secondary reservoir is not refilled at the present point in time if it can be expected that the filling volume without prior refilling is sufficient for the administration of the next following on-demand bolus.

In some embodiments, the method includes computing a set of standard infusion estimators, with each standard infusion estimator being an estimator for an amount of drug that is expected to be infused in an estimation time interval beginning at an associated predetermined time of day, and storing the set of standard infusion estimators in a memory. For such embodiment, the filling volume assessment routine includes retrieving from the memory the standard infusion estimator that is associated with the time of day corresponding to the present point in time. The retrieved standard infusion estimator is used as the infusion estimator for the prediction. By way of example, standard infusion estimators may be computed with a time interval of ten minutes, e.g., for 0:00 (midnight), 0:10, 0:20, 0:30, 0:40, 0:50, 1:00 (1 a.m.), and so forth. The times of day at which the filling volume assessment routine is carried out are also referred to assessment times of day in the following.

The standard infusion estimators are favorably pre-computed and do not need to be carried out as part of the repeatedly carried out filling volume assessment routine, with the determining and storing the set of standard infusion estimators forming an infusion estimation routine. However, the infusion estimation routine may be carried out occasionally or periodically, thereby updating or re-computing the set of standard infusion estimators. Typically, the standard infusion estimators consider both basal and bolus infusion. Each standard infusion estimator from the set of standard infusion estimators may include a standard basal infusion estimator and/or a standard bolus infusion estimator as explained in more detail further below.

Alternatively, however, an infusion estimator may be explicitly computed as part of the filling volume assessment routine each time the filling volume assessment routine is carried out.

In some embodiments, determining the estimated filling volume of the secondary reservoir is, at least in part, based on a predetermined basal infusion schedule. In therapies that include a substantially continuous drug infusion, such as CSII, basal drug infusion is normally carried out in accordance with a basal infusion schedule. The basal infusion schedule is generally predetermined and time-variable, that is, the rate of basal infusion varies as a function of time. Typically but not necessarily, the basal infusion schedule is, in CSII, a cyclic circadian schedule, having a period of 24 hours. In such case that is also assumed in the following for exemplary purposes where not stated differently, the rate of basal infusion is accordingly defined in dependence of the time of day. Typically, the basal infusion schedule is stored in a memory of an ambulatory infusion system, in particular an ambulatory infusion device control unit, by way of a lookup table that comprises the basal infusion rate for time intervals, e.g., for each hour of day or each half hour of day. It is further noted that, in a practical implementation, basal infusion is often not carried out in a continuous manner in a strict sense, but in incremental doses, with a fixed time interval of, e.g., 3 minutes or 6 minutes between successive doses. Alternatively, the incremental dose is fixed to, e.g., 0.05 IU, 0.1 IU or 0.2 IU and the time interval between successive doses is varied in accordance with the basal infusion schedule. In a further variant, a mixture or combination of both before-mentioned approaches is used. Further, the basal infusion schedule may not be stored in form of a lookup table, but in form a mathematical function respectively the parameters of such function. While it may be typically temporarily suspended or modified by a user as explained further below, basal administration is generally carried out by an ambulatory infusion system autonomously under control of an ambulatory infusion device control unit, without requiring user interaction.

Determining the estimated filling volume, based, at least in part, on a predetermined basal infusion schedule includes determining the total amount (volume) of basal infusion for the estimation time interval and subtracting this value from the filling volume of the secondary reservoir at the present point in time. The total amount of basal infusion is determined in accordance with the predetermined basal infusion schedule.

Since the basal infusion schedule is generally predetermined, the basal infusion estimator may be pre-computed in an infusion estimation routine as mentioned before. In particular, for a given start time of day and a given end time of day, a standard basal infusion estimator may be computed by summing up respectively integrating the volume of basal infusion in accordance with the basal infusion schedule for the time interval between the start time of day end the end time of day. Here, computing the estimated filling volume as part of the filling volume assessment routine simply comprises retrieving from the memory the standard basal infusion estimator in accordance with the present point in time, and subtracting this value from the filling volume of the secondary reservoir at the present point in time. Computing the standard basal infusion estimators may, for example, be carried out each time the basal infusion schedule is reprogrammed or each time the secondary reservoir is replaced. It may in particular be carried out along with computing bolus infusion estimators as explained further below.

The basal infusion schedule being predetermined means that it is generally stored and accordingly known in advance as explained before. Typically, the basal infusion schedule is programmed in accordance with the patient's respectively user's individual needs by a healthcare professional or in some cases by the patient himself as required, and may be re-programmed if needed. Because the basal infusion schedule is generally predetermined, the prediction of the filling volume of the secondary reservoir is correct, provided that basal infusion is actually carried out in accordance with the schedule. As discussed further below in more detail, this is not necessarily the case.

In some embodiments, determining the estimated filling volume includes taking into account temporary modifications of the predetermined basal infusion schedule in a time interval between the present point in time and the estimation point in time. A temporary modification of the basal infusion schedule may typically occur spontaneously and at any point in time. State-of-the-art ambulatory infusion systems allow a user to temporarily modify basal infusion for a time interval of typically a number of hours, e.g., up to for example 12 hours or 24 hours, in order to cope with special or exceptional circumstances such as physical activities or illness, and/or to temporarily suspend basal infusion. A temporarily applied basal infusion schedule that results from such modification is referred to modified basal infusion schedule. Depending on the ambulatory infusion system, the modified basal infusion schedule may be determined by proportional scaling of the basal infusion according to the predetermined schedule with a scaling factor that may be larger than one (for increased basal infusion) or smaller than one (for decreased basal infusion). In a further variant, the modified basal infusion schedule is determined as constant basal rate infusion schedule with the predetermined basal infusion schedule being temporarily replaced by the constant basal rate infusion schedule. Taking into account temporary modifications of the predetermined basal infusion schedule is achieved by replacing or modifying the predetermined basal infusion schedule with the modified basal infusion schedule for the estimation time interval or a part of the estimation time interval where the modification is active. As mentioned before, the programming or ending of the temporary modification may serve as a trigger event that forces the filling volume assessment routine to be carried out immediately, typically asynchronous with the general schedule. The same holds true for temporary modifications based on a measured and/or predicted blood glucose value as explained below.

In some embodiments, the method includes taking into account a measured and/or predicted blood glucose level for predicting the estimated filling volume. The ambulatory infusion system may include or be designed to operatively couple with a continuous glucose measurement unit that is designed to measure glucose concentration in a body fluid or body tissue in a substantially continuous way. The ambulatory infusion system may further be designed to temporarily modify the basal infusion schedule in accordance with the measured blood glucose value. It may, in particular, be designed to temporarily suspend basal infusion or reduce basal infusion according to the predetermined threshold in case of low blood glucose values. Such modification of the basal infusion schedule results in a modified basal infusion schedule as explained before in the context of user-commanded modifications and can be considered in an analogous way.

It is to be understood that a temporary modification of the basal infusion schedule may have a typically user-programmed and predetermined duration that is, e.g., selected in accordance with a planned physical activity. In embodiments where the basal infusion estimator is generally pre-computed as explained above, correspondingly modified basal infusion estimators that take into account the temporary modification may be computed at the beginning of the modification for the time span that covers the upcoming estimation points that are affected by the modification as programmed. The filling volume assessment may then use the modified basal infusion estimators for the affected time span.

Alternatively, however, the duration of the temporary modification may not be known in advance. This may in particular be the case if the temporary modification is controlled by a continuous glucose measurement unit as explained before. Here, taking into account temporary modifications of the predetermined basal infusion schedule may be achieved by determining, in the filling volume assessment routine, if a modification is active at the present point in time and using, in the affirmative case, a correspondingly modified basal infusion estimator. For this type of embodiment, the modified basal infusion estimator is accordingly computed at the present point in time, rather than at the beginning of a modification interval. It is noted that this kind of embodiment may also be used even if the duration of the modification is known. It is further noted that typically an active modification may be cancelled by the user. In this case, operation favorably proceeds based on the predetermined basal infusion schedule.

In some embodiments, determining the estimated filling volume is based, at least in part, on an expected amount, in particular, volume of on-demand bolus infusion in the time interval between the present point in time and the estimation point in time. In the context of CSII, on-demand boli are infused in order to compensate for the intake of food, in particular carbohydrates, and additionally in order to correct undesired high blood glucose values. In contrast to the basal infusion, on-demand boli are generally initiated or triggered via a dedicated user command at any point in time and may have a varying amount. On-demand boli are typically infused within a comparatively short time interval in a typical range from seconds or fractions of a second, up to a few minutes. To cope with special situations, such as the ingestion of some type of foodstuff, an on-demand bolus may also be infused over a longer time period of, e.g., an hour or up to several hours, and/or may be a combination of a portion that is infused substantially immediately and a further portion that is infused over a longer time period. Typical state-of-the-art infusion devices as used, e.g., in CSII typically offer a number of pre-defined bolus profiles (referred to, for example, as Multi Wave Bolus, Extended Bolus, etc.) from which the user may select as required in a specific situation.

Because of their typical variability in amount and infusion time, the prediction of on-demand boli is less straightforward as compared to the prediction of basal infusion. In practical application scenarios, for example in CSII, however, some predictability typically occurs. Since meals often tend to be ingested at similar points in time for different days and further often tend to be similar in size and/or composition, on-demand boli also tend to be similar.

Determining the estimated filling volume, based, at least in part, on an expected amount respectively volume of on-demand bolus infusion may include determining an expected total bolus volume from a start time to an end time, and subtracting this volume from the filling volume of the secondary reservoir at the present point in time. As explained before in the context of basal infusion, the time difference between the end time and the start time corresponds to the estimation time interval and the end time is defined by the start time plus the estimation time interval. The expected amount of on-demand bolus infusion serves as bolus infusion estimator for the bolus infusion between the start time and the end time.

Similar to a basal infusion estimator, the bolus infusion estimator may be determined in real time at the present point in time, or may be predetermined. In the latter case, the steps that are carried out at the present point in time and as part of the filling volume assessment routine are reduced to retrieving the corresponding value for the bolus infusion estimator and subtracting it from the filling volume of the secondary reservoir at the present point in time.

In some embodiments, predicting the estimated filling volume is based, at least in part, on a history of actual past infusion. A history of actual past infusion is typically stored by a history memory of an ambulatory infusion system and in particular the ambulatory infusion device control unit. Further, a history of actual past infusion may be stored in a structurally separate remote device, such as a remote controller or diabetes management device. The remote device and the ambulatory infusion device control unit are typically configured to communicate and exchange data via corresponding communication interfaces.

In some embodiments, the history of actual past infusion is stored by one or more external devices at one or more remote locations, such as a server or a cloud and are transmitted directly to the ambulatory infusion device and/or a remote controller or diabetes management device as required by way of internet communication. Further, infusion estimators, in particular standard infusion estimators, may be pre-computed and stored by such external device(s).

In some embodiments, a history stores the time and amount of each liquid drug infusion, being it the infusion of an on-demand bolus or an incremental basal infusion in accordance with the basal infusion schedule, together with a time stamp (the time stamp providing information regarding the time of day and favorably also the date). Since, however, basal administration is generally carried out according to a predetermined basal infusion schedule and at predetermined points in time (such as every three minutes, starting at 0:00), the history of past basal infusion can be determined from the basal infusion schedule, provided that no events have occurred which temporarily influence the basal infusion.

The history of on-demand boli is stored by way of a list of time stamps and bolus amounts $(t_i, B_i)$, with i being an index value, $t_i$ being the time stamp of a past bolus infusion and $B_i$ being the corresponding bolus amount. If the ambulatory infusion device offers different types of on-demand boli as explained before, further relevant data such as an identifier of the bolus type, the volumes which are infused immediately and over the longer time period as well as the time period over which the infusion is carried out, are stored.

A history of actual past infusion is particularly advantageous for determining a bolus infusion estimator as explained before. A bolus infusion estimator for a given start time as time of day may be obtained by way of statistical evaluation of actual past bolus infusions for an interval starting with the start time and ending with the start time plus the estimation time as end time. The statistical evaluation may include one or favorably a number of days. The determination of the bolus infusion estimator may consider the last preceding day or, preferably, a number of preceding days, such as 7, 14, or 30 days. The determination may be computed each time directly from the volumes of past bolus infusions, or may be computed by modifying a previously computed estimator. In some embodiments, all past days that are used for the computation are weighted equally. In alternative embodiments, however, different days are weighted differently. In particular, days of the recent past may be considered with a higher weight as compared to days of the more distant past.

As bolus infusion estimator, a predetermined percentile of bolus infusion volumes for the considered past days, such as the $80^{th}$ percentile or the $90^{th}$ percentile or $100^{th}$ percentile may be used, with the $100^{th}$ percentile being the maximum bolus infusion volume for the considered past days and time interval from start time to end time. It is noted that other static measures that are known in the art, e.g., based on mean and variance, may be used as well.

In some embodiments, determining the bolus infusion estimator based on a history of actual past infusion for a number of past days considers a continuous sequence of past days. Alternatively, however, only selected days may be considered. For example, bolus infusion estimators may be computed separately for all days or the week, or separately for working days and weekends. Such embodiments may be advantageous in case the typical bolus infusion pattern is substantially different for different days. In further embodiments, a user input may be provided for the exclusion of particular days from the computation, such as days of illness, traveling, or general exceptional circumstances. This type of embodiment is particularly favorable if only a small number of days is used for computation, resulting in the infusion history of each day having significant impact on the computation.

If the bolus infusion estimator is not computed in real time each time the filling volume assessment routine is carried out, that is, at the present point in time, it may be computed, e.g., once a day, once a week, or along with replacing the secondary reservoir.

It is noted that, similar to computing the bolus infusion estimator separately for different days, basal infusion estimators may be computed separately for different days. Typical state of the art ambulatory infusion systems allow the definition of different basal infusion schedules between which the user may switch or the system may switch automatically, to cope, e.g., with the difference between day shift and night shift, and/or between working days and weekends. Basal infusion estimators may be determined separately for the different basal infusion schedules.

Alternatively to determining a bolus infusion estimator based on a history of actual past infusion as explained before, a bolus infusion estimator may be pre-computed based, e.g., on a diabetic's nutrition schedule and may be stored in a memory of the ambulatory infusion system, e.g., by way of a lookup table for the single times of days at which the determination is carried out, with the single times of days serving as start times.

In a further variant, both of the before-mentioned approaches are combined and bolus infusion estimators are predefined, e.g., based on a nutrition schedule, when an ambulatory infusion device is set-up respectively initialized after supply to a user, or in case the nutrition schedule is fundamentally changed. Subsequently, the estimators are amended or modified based on the history of actual past infusion.

In embodiments that include computing a set of standard basal infusion estimators for predetermined assessment times of day, the set of standard basal infusion estimators may include a basal infusion estimator for each assessment time of day, e.g., for 0:00, 0:10, 0:20, and so forth.

In embodiments that involve computing a set of standard bolus infusion estimators for predetermined assessment times of day as explained before, a bolus infusion estimator may be computed for each of the assessment times of day, e.g., for 0:00, 0:10, 0:20 and so forth, like for the basal infusion.

A set of pre-computed infusion estimators may accordingly be represented by a table respectively a list of triples, each triple comprising an assessment time of day, $T_j$, a corresponding pre-computed basal infusion estimator $b^*_j$ and a corresponding pre-computed bolus infusion estimator $B^*_j$, with j being an index.

Since on-demand bolus infusion is, however, typically carried out at similar times of day (correlated with the meal times) but with some variability, the method may include determining, from a history of actual past bolus infusions, typical bolus administration times of day and associated typical bolus volumes. Typical bolus administration times of day $T_j$ and typical bolus volumes $B^*_j$ may be determined from the history of actual past bolus infusion using statistical or pattern recognition algorithms known in the art. The set of typical bolus administration times of day and associated typical bolus volumes may be stored in a list of pairs $(T_j, B^*_j)$ that may, e.g., have three to five entries (corresponding to the number of meals/snack) for typical days. When carrying out the filling volume assessment routine at the present point in time, only those typical bolus volumes $B^*_j$ may be considered which lay in the time interval between the present point in time and the future estimation point in time, as indicated by the corresponding typical bolus administration time of day $T_j$.

In some embodiments that include determining the estimated filling volume based, at least in part, on an expected amount respectively volume of on-demand bolus infusion, the method may include ignoring selected past boli. In this way, on demand boli that are administered for the purpose of lowering a raised blood glucose value may be excluded for the purpose of the estimation since they are only required sporadically and typically do not follow a defined schedule. For this purpose, a corresponding marker may be stored in a history along with the bolus amount and the time stamp as explained before. Similarly, a bolus may optionally be marked as exceptional for other reasons and also ignored respectively excluded for the computation.

In typical embodiments, both expected basal infusion and expected bolus infusion are considered by subtracting the corresponding amounts from the filling volume at the present point in time. Here, determining, at a present point in time, the estimated filling volume of the secondary reservoir at the future estimation point in time includes subtracting the basal infusion estimator and the bolus infusion estimator from the present filling volume at the present point in time.

In a further aspect, the overall objective is achieved by a refilling scheduling unit. The refilling scheduling unit is configured to carry out a method for scheduling a refilling of a secondary reservoir according to any embodiment as described before and/or further below. The refilling scheduling unit may be realized by respectively may be based on a microcomputer and/or microcontroller. While a computer-implemented embodiment is further assumed in the following for exemplary purposes, it is not essential. A refilling scheduling unit that is configured to carry out a method in accordance with the present disclosure may also be realized, fully or partly, by other types of circuitry and based, e.g., on an ASIC.

In a further aspect, an ambulatory infusion device control unit is configured to control operation of an ambulatory infusion device. The ambulatory infusion device control unit includes a valve control unit, the valve control unit being configured to control actuation of a valve actuator to switch a valve unit between a filling state and an alternative dosing state. The ambulatory infusion device control unit further includes a secondary reservoir actuator control unit, the secondary reservoir actuator control unit being configured to control operation of a secondary reservoir actuator to operate in a filling mode and to increase a fluidic volume of a secondary reservoir in the filling mode, and to alternatively operate in a dosing mode and to decrease the fluidic volume of the secondary reservoir in the dosing mode in a metering manner and in a plurality of incremental steps over an extended time period.

The ambulatory infusion device control unit further includes a refilling scheduling unit according to any embodiment as described before and/or further below. The refilling scheduling unit is configured to operate in parallel with the secondary reservoir actuator control unit in the dosing mode.

The ambulatory infusion device control unit is further configured, if the method for scheduling the refilling of the secondary reservoir determines that the secondary reservoir shall be refilled, to control execution of a secondary reservoir refilling procedure, the secondary reservoir refilling procedure including a sequence of: (i) controlling the valve actuator to switch the valve unit from the dosing state into the filling state; (ii) controlling the secondary reservoir actuator to increase the fluidic volume to a given filling volume; (iii) controlling the valve actuator to switch the valve unit from the filling state into the dosing state.

In some embodiments, the primary reservoir is a typically, but not necessarily, cylindrical cartridge, typically a glass cartridge, with a sealing displaceable cartridge piston that is displaced inside the cartridge body when emptying the primary reservoir. It is known that the cartridge piston, typically a rubber piston, of such liquid drug cartridges tends to stick if it is not moved respectively displaced for a longer time period, and subsequently requires a considerable break-loose force. In the context of the here-assumed architecture with a primary reservoir and a secondary reservoir, the cartridge piston moves only for the refilling of the secondary reservoir. In dependence of the user's individual insulin demand, this time period between consecutive refilling operations may be comparatively long, typically several hours, up to a day or more. It is further to be understood that, when refilling the secondary reservoir, liquid drug is sucked out of the primary reservoir and the cartridge piston moves only via a pulling force as a result of the sucking pressure that is exerted by the liquid drug on its liquid-contacting front surface. Favorably, no or only little additional pushing force is applied on the cartridge piston. It is further to be understood that the required break-loose force to overcome the sticking may be in the same range or even be larger than the maximum force that can be applied by the sucking pressure. Consequently, sticking is an issue of concern.

In a further aspect, this disclosure teaches reducing and preferably avoiding the before-explained problem of a sticking cartridge piston, by a piston sticking prevention method. The piston sticking prevention method includes, in the dosing state, comparing the time that has lapsed since the refilling of the secondary reservoir with a predetermined back-dosing time interval. The piston sticking prevention method further includes, if it is determined that the back-dosing time interval has lapsed, controlling a valve actuator to switch the valve unit from the dosing state into the filling state, followed by controlling the secondary reservoir actuator to decrease the fluidic volume of the secondary reservoir by a back-dosing volume, followed by controlling the valve actuator to switch the valve unit back from the filling state into the dosing state. According to a further aspect, the problem of preventing sticking of a cartridge piston is solved by an ambulatory infusion device control unit that is configured to execute a piston sticking prevention method.

By decreasing the fluidic volume of the secondary reservoir, an amount of liquid drug that corresponds to the back-dosing volume is forced from the secondary reservoir into the primary reservoir. In this process, a pushing force is accordingly exerted by the liquid drug onto the cartridge piston, thereby overcoming the sticking friction and the break-loose force. It is noted that during the back-dosing, no liquid drug is infused into the patient's body. The back-dosing volume is comparatively small may, e.g., be in a range of 1 IU to 5 IU. The back-dosing time interval is favorably somewhat shorter than a time interval beyond which sticking can be expected to occur and may, for example, be 12 hours in an exemplary embodiment.

The piston sticking prevention method may be carried out repeatedly or continuously in parallel and independent from the method for scheduling the refilling. In alternative embodiments, however, it may be carried out in a coordinated way with the method for scheduling the refilling. It may in particular be carried out if it is determined that the secondary reservoir shall not be refilled at the present point in time.

It is noted that the disclosed sticking-friction prevention method is in principle independent and distinct form the refilling scheduling method and may optionally be implemented and carried out without some or all of the other method steps. Similarly, an ambulatory infusion device control unit may be configured to execute a sticking-friction prevention method, without being necessarily configured to carry out all or some of the steps of the method for scheduling the refilling of the secondary reservoir.

In a further aspect, a computer program product including a non-transient computer readable medium can be provided. The non-transient computer readable medium has stored therein a computer program code configured to direct a processor to execute a method for scheduling a refilling of a secondary reservoir of an ambulatory infusion system and/or to act as refilling scheduling unit and/or an ambulatory infusion device control unit according to any embodiment as described above and/or further below. The processor may in particular by realized or may be formed by one or more microprocessors and/or microcontrollers.

In a further aspect, the ambulatory infusion device includes an ambulatory infusion device control unit as discussed above. The ambulatory infusion device further includes a valve actuator in operative coupling with the valve control unit and a secondary reservoir actuator in operative coupling with the secondary reservoir actuator control unit. The valve actuator and the secondary reservoir actuator are typically electrical actuators such as rotary actuators, in particular DC motors, brushless DC motors or stepper motors. Other type of electric actuators may also be used, in particular, a shape memory alloy actuator as valve actuator. The valve actuator is designed to releasable operatively couple and engage a valve unit. The secondary reservoir actuator is designed to releasably operatively couple and engage a piston that is received in a dosing cylinder as explained below, with the piston and the dosing cylinder forming a metering pump unit. The metering pump unit and the valve unit form, in combination, a dosing unit and are realized as common integral unit. The dosing cylinder and the piston further form a secondary reservoir of controlled variable volume.

Generally, a method in accordance with any disclosed embodiment may be carried out by way of a corresponding embodiment of a refilling scheduling unit, ambulatory infusion device, ambulatory infusion device control unit and/or a computer program product which is accordingly also disclosed. Similarly, refilling scheduling units, ambulatory infusion device control units, ambulatory infusion devices and computer-program products in accordance with disclosed embodiments may be used to carry out a corresponding method embodiment, which are accordingly also disclosed.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
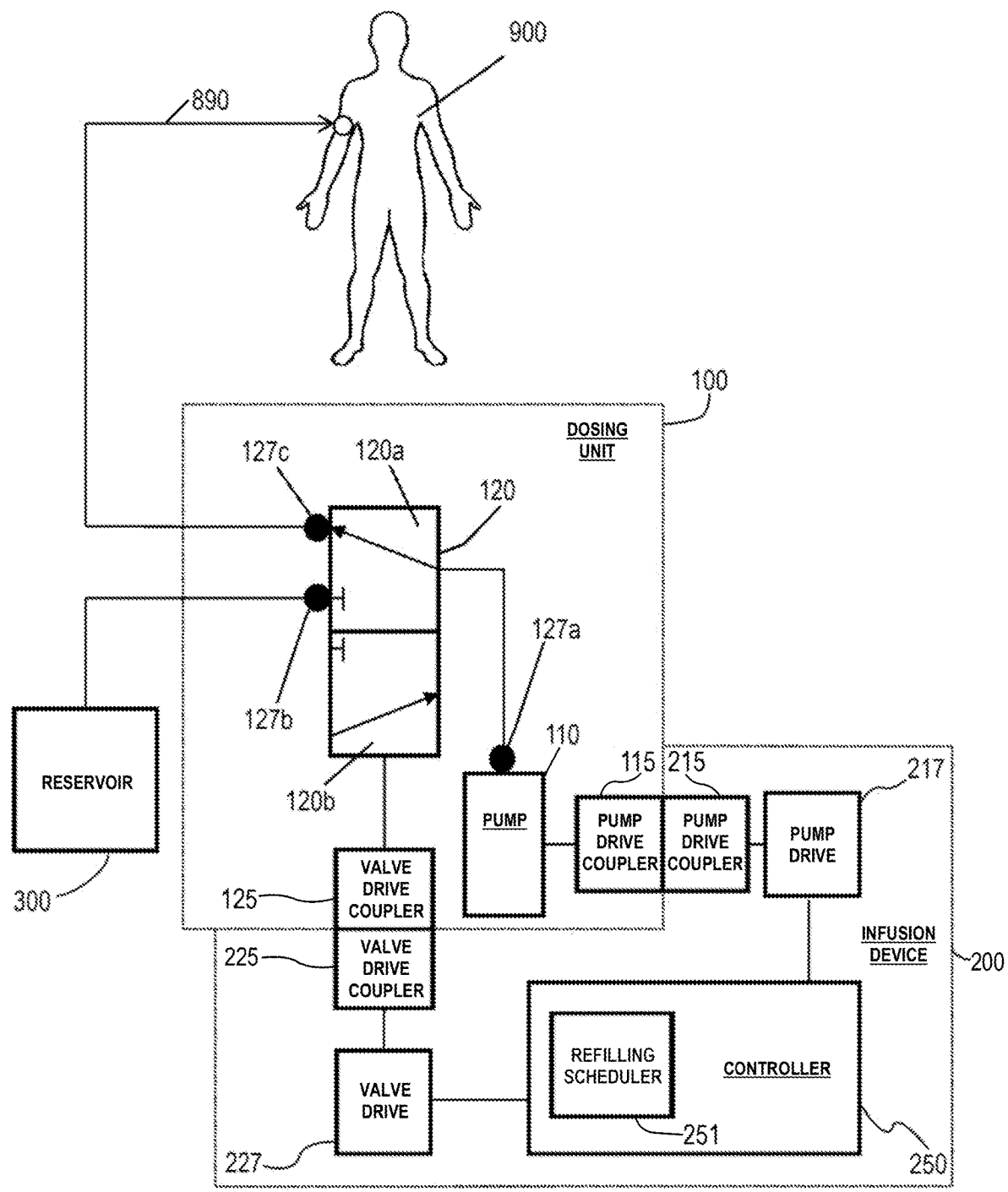
FIG. 1 shows major components of an ambulatory infusion system in a simplified functional view.

In the following, reference is first made to FIG. 1. FIG. 1 shows a dosing unit 100, an ambulatory infusion device 200, and a liquid drug reservoir 300. It is to be noted that only those structural and functional units are shown that are of particular relevance in the context of the present disclosure.

The dosing unit 100 includes a metering pump unit (or pump) 110, including a dosing cylinder with a bore and a piston (elements not separately referenced) as described above in the general description. In a proximal front wall of the dosing cylinder, a bore is arranged as fluidic port that couples to the pump port 127*a*. The dosing unit further includes a valve unit (or valve) 120 that may alternatively be in a filling state, 120*b* or in a dosing state 120*a*. During operation, the valve unit 120 is repeatedly switched between those states. The reservoir 300 is fluidically coupled to the valve unit 120 via a filling port 127*b*. The patient 900 is fluidically coupled to the valve unit via a dosing port 127*c* and infusion site interface 890. It is noted that the infusion site interface 890 is exemplarily shown as integral with an infusion line, e.g. a catheter. The dosing unit 100 further includes a valve driver coupler 125 for switching the valve unit 120 between the filling state 120*b*, and the dosing state 120*a*. Similarly, the dosing unit 100 includes a pump driver coupler 115 for moving the piston of the pump unit 110 linearly inside the dosing cylinder. In an exemplary embodiment, the maximum filling volume of the dosing cylinder is 7 IU (International Units) of a liquid insulin formulation with concentration U100, respectively 70 microliter.

With respect to the valve unit 120, it is further noted that FIG. 1 only shows the states 120*a*, 120*b* where either of the filling port 127*b* or the dosing port 127*c* is coupled to the pump port 127*a*. In a further intermediate state, however, all three ports 127*a*, 127*b*, 127*c* are closed, resulting in fluidic isolation.

The ambulatory infusion device includes a pump drive 217 that is coupled to a pump drive coupler 215 as well as a valve drive 227 that is coupled to a valve drive coupler 225. The pump drive 217 and the valve drive 227 are powered and controlled by an electronic ambulatory infusion device control unit (controller) 250 that is typically based on one or more microcontrollers and/or microprocessors.

The dosing cylinder and the piston form in combination a secondary reservoir, while the liquid drug reservoir 300 forms a primary reservoir and may be realized by a cylindrical cartridge with sealing displaceable cartridge piston, or may be a fully or partly flexible reservoir, such as a pouch. The primary reservoir may be provided readily filled by a manufacturer, or may be user-filled. The ambulatory infusion device control unit 250 further includes a secondary reservoir actuator control unit (not separately referenced) that controls operation of the pump drive 217 as secondary reservoir actuator. Further, the ambulatory infusion device control unit 250 includes a valve actuator control unit (not separately referenced) that controls operation of the valve drive 227 as valve actuator. The ambulatory infusion device control unit 250 further includes a refilling scheduling unit 251 in accordance with the present disclosure, operation of which is further explained in more detail below.

It is noted that the liquid drug reservoir 300 and the dosing unit 100 are shown as distinct from the ambulatory infusion device 200. They may be and typically are, however, in an operational configuration mechanically coupled to the ambulatory infusion device 200 to form a common, compact unit, and/or may be inserted into corresponding compartments of the ambulatory infusion device housing. Further, the dosing unit 100 and the liquid drug reservoir 300 may be realized as common unit in some embodiments.

Figure 2:
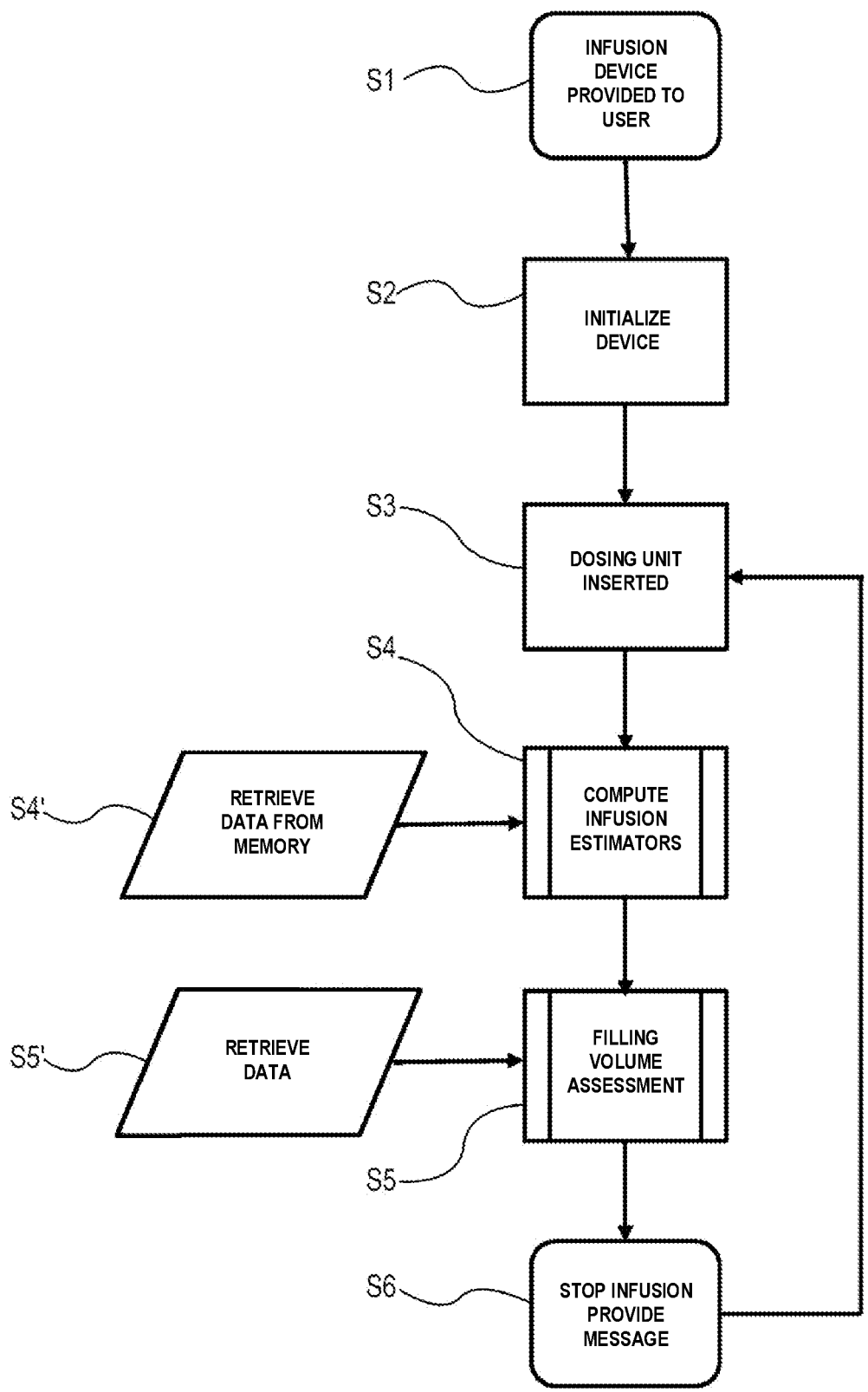
FIG. 2 shows an operational flow in accordance with the present disclosure.
Figure 3:
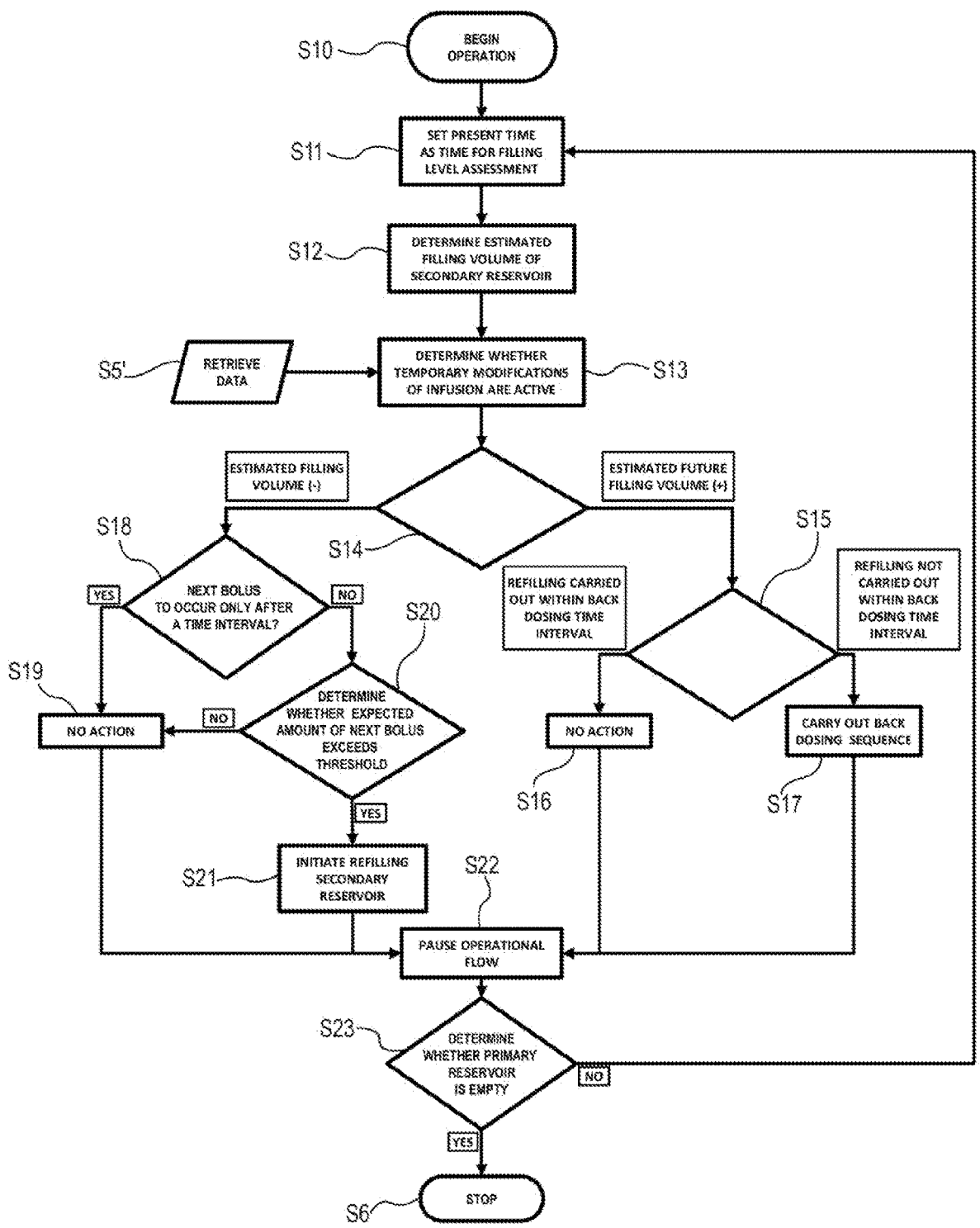
FIG. 3 shows a further operational flow of a refilling scheduling method in accordance with the present disclosure.

In the following, reference is additionally made to FIG. 2, illustrating an exemplary method in accordance with the present disclosure. The method starts in step S1 where a new ambulatory infusion device is provided to a user, e.g., a Person with Diabetes (PwD). The ambulatory infusion device is designed to be used in combination with a primary reservoir and a secondary reservoir as explained before. It is noted that the methods that are illustrated in FIGS. 2, 3 are based on a setup with an ambulatory infusion device 200 and a dosing unit 100 and its components as illustrated in FIG. 1 and explained before.

In subsequent parameter setting step S2, the ambulatory infusion device is prepared and initialized for use by the user. This in particular includes the programming of the basal administration schedule or a number of basal administration schedules, e.g., for working days and for weekends, as explained before. In many state-of-the-art systems, the ambulatory infusion device comprises or is adapted to operatively couple to a bolus recommendation system. A bolus recommendation system is designed to compute and propose to the user bolus volumes of drug boli, in particular insulin boli, that are appropriate for covering an amount of food intake, in particular carbohydrate intake, and/or for lowering undesirably raised blood glucose values. The computation depends on the amount and potentially type of food and/or the blood glucose value, using a number of patient-specific bolus computation parameters that are also set respectively programmed in step S2. If the ambulatory infusion device that has been provided in step S1 is a replacement device for a previously used device, step S2 may comprise or consist of retrieving the one or more basal administration schedules and bolus computation parameters from the previously used device respectively from a data file storing such parameters.

In subsequent maintenance step S3, a dosing unit with a secondary reservoir as well as a primary reservoir are inserted into the ambulatory infusion device and coupled with an infusion cannula directly or via infusion tubing. Further, additional steps that are required in the context of exchanging the dosing unit and/or the secondary reservoir are carried out, such as priming. Here it is assumed that the primary reservoir and the dosing unit with the secondary reservoir are generally exchanged along with each other, e.g., every few days up to every few weeks, depending on the user's individual requirements. The dosing unit and the primary reservoir may also be formed as common integral unit. Alternatively, however, they may be structurally separate and also exchanged separately from each other.

In subsequent step S4, standard infusion estimators are computed for use during regular operation. The standard infusion estimators include a set of standard basal infusion estimators and a set of standard bolus infusion estimators. By way of example, the estimation time interval is predetermined as two hours, and both a standard bolus estimator and a standard basal estimator are computed for specific times of day with an interval of 10 minutes, that is, for 0:00 (midnight), 0:10, 0:20, 0:30, 0:40, 0:50, 1:00 (1 a.m.), and so forth. The set of standard basal infusion estimators are computed based on the basal infusion schedule. Alternatively to a computation based on the basal infusion schedule as programmed, the basal infusion estimators may be computed based on actual past basal infusion as stored in a history memory. This approach has the advantage that typical temporary modifications that occurred in the past are also taken into account. The set of standard bolus infusion estimators is computed based on a history of actual past bolus infusions that is stored in a history memory of the ambulatory infusion device itself and/or an external device, such as a remote controller or diabetes management device. For the computation, the data are retrieved from the history memory (Step S4'). For each time of day as start time for which the computation is carried out, the corresponding bolus infusion estimator is computed as, e.g., $80^{th}$ percentile, as explained before in the general description. The computation is, e.g., carried out based on a number of, e.g., three or seven past days.

Subsequent to steps S4, S4', regular liquid drug infusion is carried out. As background process, a filling volume assessment procedure is repeatedly and automatically carried out (steps S5, S5') that are explained further below in more detail.

If, during regular operation, the primary reservoir becomes empty, the operational flow proceeds with step S6 where infusion is stopped and a corresponding message is provided. From step S6, the operational flow returns to the maintenance routine S3. Favorably, one or more warnings are provided well before the primary reservoir is actually empty, allowing the user to go to the maintenance step S3 and exchange the dosing unit and the primary reservoir at a convenient point in time.

In the following, reference is additionally made to FIG. 3, showing the operational flow of steps associated with the scheduling of the refilling, as well as a further related step during regular operation of the ambulatory infusion device.

In step S10, regular operation of the ambulatory infusion device is started, i.e., the ambulatory infusion device is operated to autonomously infuse liquid drug according to the basal administration schedule and additional boli on demand.

In subsequent step S11, the present point in time is set as time for carrying out a filling level assessment. In subsequent step S12, the estimated filling volume of the secondary reservoir is determined.

In embodiments where a sets of standard bolus infusion estimators and standard basal infusion estimators have been computed in advance, step S12 comprises retrieving the standard basal infusion estimator and the standard bolus estimator that are associated with the present point in time and determining the estimated filling volume by subtracting the standard basal estimator and the standard bolus estimator from the current filling volume of the secondary reservoir. In alternative embodiments where no standard infusion estimators have been computed in advance, the estimated filling volume of the secondary reservoir may be computed in step S12 as explained in the general description, using the present point in time as start point and the present point in time plus the estimation time interval as end time.

In subsequent step S13, it is determined whether any temporary modifications of the infusion are active. Data regarding such temporary modification may be retrieved (step S5') from a continuous glucose measurement device or continuous glucose measurement unit, and/or from a memory of the ambulatory infusion device that stores information regarding temporary modifications. If such modification is active, step S13 further includes modifying or updating the estimated filling volume of the secondary reservoir accordingly.

In subsequent step S14, the operational flow branches in dependence of the estimated filling volume.

If the estimated filling volume at the future estimation point in time is positive, the operational flow proceeds with step S15. Here it is accordingly assumed that the secondary reservoir will not become empty within the estimation time interval. In this case, optional steps S15, S16, S17 are carried out.

In step S15, the time that has lapsed since the last refilling of the secondary reservoir is assessed by way of comparison with a predetermined back-dosing time interval of, e.g., 12 hours, and the operational flow branches in dependence of the result. If a refilling has been carried out within the back-dosing time interval, the operational flow proceeds with step S16 where no action is required. Otherwise, a back-dosing sequence is carried out in step S17.

In the back-dosing sequence, the valve actuator is controlled to switch from the dosing state into the filling state. Subsequently, the secondary reservoir actuator is, while in the dosing mode, controlled to decrease the fluidic volume of the secondary reservoir by a small back-dosing volume. Subsequently, the valve actuator is controlled to switch back from the filling state into the dosing state. By decreasing the fluidic volume of the secondary reservoir, an amount of liquid drug that corresponds to the back-dosing volume is forced from the secondary reservoir into the primary reservoir. For the primary reservoir being a glass or plastic cartridge with a cartridge piston that is sealing and movable arranged in a glass cartridge body, this is associated with a forced movement of the cartridge piston inside the cartridge body against its regular movement direction for emptying the cartridge, the forced piston movement being associated with a pushing force that is exerted onto the cartridge by the liquid drug. In this way, a breakaway force between cartridge piston and cartridge body that typically builds up if the piston is not moved for some time, is overcome. Such breakaway force may be considerable and well above a pulling force that may be fluidically exerted on the piston by drawing liquid out of the cartridge. It is noted that the method steps associated with the back-dosing may also be independently implemented as a piston-sticking prevention method.

After either of step S16 or step S17, the operational flow proceeds with step S22 as explained further below.

In alternative embodiments where the breakaway force is particularly low, or in embodiments where another type of primary reservoir such as a pouch is used, steps S15, S16, and S17 may not be required.

If the estimated filling volume at the end time is negative, the operational flow proceeds, following step S14, with step S18. In step S18, it is determined whether a next following bolus infusion is expected to occur only after a time interval as defined by a bolus timeout threshold from the present point in time. The bolus timeout threshold may be 20 min in a specific example, but longer or shorter values may be used as well. In the affirmative case, the operational flow proceeds with step S19 where it is determined that no action is presently required. Otherwise, the operational flow proceeds with step S20 where it is determined whether the expected amount of the next following bolus exceeds a bolus volume threshold. Favorably, the bolus volume threshold is dynamically set to the present filling volume of the secondary reservoir. In the negative case, the operational flow also proceeds with step S19. Otherwise, the operational flow proceeds with step S21 where a refilling of the secondary reservoir is initiated.

After carrying out either of step S19 or step S21, the operational flow proceeds with step S22. In step S22, the operational flow pauses until the present point in time corresponds to the time for the next subsequent execution of the filling volume assessment routine. In subsequent step S23, it is determined whether the primary reservoir is empty. In the affirmative case, the operational flow proceeds with step S6, where the algorithm terminates and a replacement routine for the primary reservoir and optionally the dosing unit with the secondary reservoir is initiated. In the negative case, the operational flow returns to step S11 for the next execution of the filling volume assessment routine.

It is noted that, like steps S15, S16, S17, the steps S18, S19, S20 are optional. Via steps S18, S19, an otherwise initiated refilling is avoided in situations where it may in fact be unnecessary due to typical variability in drug infusion, as explained in the general description. Via additional step S20, a refilling is avoided at the present point in time in situations where the next expected on-demand bolus may still be infused without prior refilling.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A method for managing refilling of a secondary reservoir of an ambulatory infusion system from a primary reservoir that stores a liquid drug, the method including repeatedly and automatically carrying out a filling volume assessment routine, comprising:
   (a) determining at a present time an estimated filling volume of the secondary reservoir at a future time, wherein the future time occurs after an estimation time interval passes after the present time;
   (b) determining based on the estimated filling volume if the secondary reservoir shall be refilled at the present time; and
   (c) when the determination of step (b) is that the secondary reservoir shall be refilled, refilling the secondary reservoir at the present time.

2. The method according to claim 1, further comprising determining that the secondary reservoir shall be refilled when the estimated filling volume is below a filling volume threshold.

3. The method according to claim 1, further comprising determining that the secondary reservoir shall not be refilled if the estimated filling volume is below a filling volume threshold and an expected duration to a next administration of an on-demand bolus exceeds a bolus timeout threshold.

4. The method according to claim 1, further comprising determining that the secondary reservoir shall not be refilled when (i) the estimated filling volume is below a filling volume threshold, (ii) the expected duration to the next administration of an on-demand bolus does not exceed a bolus timeout threshold, and (iii) an expected bolus volume of the next on-demand bolus does not exceed a bolus volume threshold.

5. The method according to claim 1, wherein the filling volume assessment routine includes determining the estimated filling volume by subtracting an infusion estimator for an amount of the liquid drug that is expected to be infused in the estimation time interval from the filling volume of the secondary reservoir at the present time.

6. The method according to claim 1, further comprising computing a set of standard infusion estimators, each standard infusion estimator being an estimator for an amount of the liquid drug that is expected to be infused in a standard estimation time interval beginning at an associated predetermined time of day, and storing the set of standard infusion estimators in a memory, wherein the filling volume assessment routine includes retrieving from the memory the standard infusion estimator that is associated with the time of day corresponding to the present time.

7. The method according to claim 1, wherein determining the estimated filling volume is based, at least in part, on a predetermined basal infusion schedule.

8. The method according to claim 7, wherein determining the estimated filling volume includes taking into account temporary modifications of the predetermined basal infusion schedule during the estimation time interval.

9. The method according to claim 1, wherein determining the estimated filling volume is based, at least in part, on an expected amount of on-demand bolus infusion in the estimation time interval.

10. The method according to claim 1, wherein predicting the estimated filling volume is based, at least in part, on a history of actual past infusion.

11. The method of claim 1, further comprising taking into account a measured and/or predicted blood glucose level for predicting the estimated filling volume.

12. The method according to claim 1, further comprising carrying out the filling volume assessment routine at time intervals of a duration that is shorter than the estimation time interval.

13. A refilling scheduling unit configured to carry out a method according to claim 1.

14. A method for managing refilling of a secondary reservoir of an ambulatory infusion system from a primary reservoir that stores a liquid drug, the method including repeatedly and automatically carrying out a filling volume assessment routine comprising the following steps:
   (a) determining at a present time an estimated filling volume of the secondary reservoir at a future time, wherein the future time occurs after an estimation time interval passes after the present time;
   (b) determining based on the estimated filling volume if the secondary reservoir shall be refilled at the present time, wherein the filling volume assessment routine is carried out at least twice during the estimation time interval; and
   (c) when it is determined the determination of step (b) is that the secondary reservoir shall be refilled, refilling the secondary reservoir at the present time.

15. The method according to claim 14, further comprising determining that the secondary reservoir shall be refilled when the estimated filling volume is below a filling volume threshold.

16. The method according to claim 14, further comprising determining that the secondary reservoir shall not be refilled if the estimated filling volume is below a filling volume threshold and an expected duration to a next administration of an on-demand bolus exceeds a bolus timeout threshold.

17. The method according to claim 14, further comprising determining that the secondary reservoir shall not be refilled when (i) the estimated filling volume is below a filling volume threshold, (ii) the expected duration to the next administration of an on-demand bolus does not exceed a bolus timeout threshold, and (iii) an expected bolus volume of the next on-demand bolus does not exceed a bolus volume threshold.

18. The method according to claim 14, wherein the filling volume assessment routine includes determining the estimated filling volume by subtracting an infusion estimator for an amount of the liquid drug that is expected to be infused in the estimation time interval from the filling volume of the secondary reservoir at the present time.

19. The method according to claim 14, further comprising computing a set of standard infusion estimators, each standard infusion estimator being an estimator for an amount of the liquid drug that is expected to be infused in a standard estimation time interval beginning at an associated predetermined time of day, and storing the set of standard infusion estimators in a memory, wherein the filling volume assessment routine includes retrieving from the memory the standard infusion estimator that is associated with the time of day corresponding to the present time.

20. The method according to claim 14, wherein determining the estimated filling volume is based, at least in part, on a predetermined basal infusion schedule.

21. The method according to claim 20, wherein determining the estimated filling volume includes taking into account temporary modifications of the predetermined basal infusion schedule during the estimation time interval.

22. The method according to claim 14, wherein determining the estimated filling volume is based, at least in part, on an expected amount of on-demand bolus infusion in the estimation time interval.

23. The method according to claim 14, wherein predicting the estimated filling volume is based, at least in part, on a history of actual past infusion.

24. The method of claim 14, further comprising taking into account a measured and/or predicted blood glucose level for predicting the estimated filling volume.

25. A refilling scheduling unit configured to carry out a method according to claim 14.

* * * * *